| United States Patent [19] | [11] | 4,310,329 |
|---|---|---|
| Holland | [45] | Jan. 12, 1982 |

[54] AQUEOUS COMPOSITIONS FOR DARKENING KERATINOUS MATERIALS

[75] Inventor: David O. Holland, Dorking, England

[73] Assignee: Combe Incorporated, White Plains, N.Y.

[21] Appl. No.: 239,476

[22] Filed: Mar. 2, 1981

[51] Int. Cl.³ ............................ D06P 3/14; D06P 3/30
[52] U.S. Cl. ........................................ 8/404; 8/405; 8/604; 8/636
[58] Field of Search ........................... 8/404, 405, 604

[56] References Cited

U.S. PATENT DOCUMENTS 3,954,393  5/1976  Lapidus .................................. 8/598
4,195,972  4/1980  Lapidus .................................. 8/405

*Primary Examiner*—Maria Parrish Tungol
*Attorney, Agent, or Firm*—Roland T. Bryan

[57] ABSTRACT

Aqueous compositions for darkening keratinous material, particularly hair, comprise a mixture of a solution of a salt of thiosulphuric acid, preferably in an amount of 0.2–5.0% by weight as thiosulphate ion, preferably as the sodium thiosulphate or an amine such as triethanolamine thiosulphate; with a solution of a complex of bismuth with an amino-polyacetic acid such as nitrilotriacetic acid or ethylenediamine tetracetic acid, the bismuth preferably being present in an amount (measured as carbonate) of 0.1–5.0% by weight; in the presence of a water-soluble amine, preferably an a alkanolamine such as mono-, di- or triethanolamine in an amount to maintain the pH in the range 8 to 11; and of a di- or poly-hydroxy humectant, preferably glycerol or propylene glycol in an amount of 5–70% by weight.

13 Claims, No Drawings

AQUEOUS COMPOSITIONS FOR DARKENING KERATINOUS MATERIALS

Solutions of salts of bismuth have been used to darken human hair and other keratinous matter for many years. For example, British Pat. No. 1,467,874 provides a hair-dyeing composition comprising sulphur and the water-soluble reaction product of bismuth citrate and triethanolamine in an aqueous vehicle. However, the rate at which these solutions react with the hair to produce the dark colour is slow, and many such formulations are not stable and need to be freshly prepared before use. Sulphur and sodium thiosulphate have been recommended to hasten the darkening process, but the rate at which hair is darkened has nevertheless hitherto been unsatisfactory. Lead salts have also been used in hair darkening compositions; but the same problems arise and in addition the known toxicity of lead is a disadvantage.

It is an object of the present invention to provide aqueous compositions containing bismuth which are able to darken keratinous materials such as wool and fur and, particularly, hair and which are at the same time stable.

The present invention provides an aqueous composition for darkening keratinous material comprising a mixture of a solution of a salt of thiosulphuric acid, with a solution of a complex of bismuth with an amino-polyacetic acid, in the presence of a water-soluble amine, and of a di- or poly-hydroxy humectant. Preferably the aqueous composition comprises from 0.21 to 5.0% by weight of thiosulphate ion ($S_2O_3=$), from 0.1 to 5.0% by weight of bismuth (as carbonate), water-soluble amine to maintain the pH in the range 8-11 and from 5 to 70% by weight of the humectant.

The amino-polyacetic acid used as a complexing agent for bismuth may suitably be nitrilotriacetic acid (NTA) or ethylenediamine tetracetic acid (EDTA), EDTA being preferred. The method of preparation of the complex is not critical. According to one method, 10 parts of bismuth carbonate or bismuth oxycarbonate or the equivalent quantity of bismuth oxide may be suspended in water with either 12.5 parts of EDTA or 13.6 parts of NTA, the suspension heated, and a water-soluble amine added slowly with stirring until virtually all the solid matter has dissolved.

The composition of the invention preferably contains 0.1 to 5% by weight, particularly 0.25 to 1.5% by weight of bismuth, expressed as carbonate. The amount of complexing agent (e.g. EDTA) used should preferably be no more than is necessary to form a water-soluble complex, since an excess appears to decrease the efficiency of the composition for darkening hair.

While the nature of the water-soluble amine is not critical, we have found that alkanolamines are particularly effective. Among these may be used monoethanolamine, diethanolamine, triethanolamine and tri-isopropanolamine. One of these alkanolamines may be used to complete preparation of the water-soluble bismuth complex as described above. In addition, it is preferred to include a further amount of alkali, preferably a water-soluble amine in an amount from 1-10%, particularly 2-5%, of the composition. The amount of excess alkali used should preferably be such as to bring the final pH of the composition to a value in the range 8-11, preferably 8-10.5. Compositions of the invention preferably have a pH in the range 6-11, particularly 8-10.5.

As a di- or poly-hydroxy humectant, propylene glycol is preferred, although glycerol or polyethylene glycol may be used. The nature and proportion of the humectant materially affects the speed of darkening achieved by the composition. Thus for example, glycerol may be used to produce brown colours rapidly up to a concentration of about 30%. Above that level it has an increasingly deleterious effect. Propylene glycol on the other hand is particularly effective in promoting colour production in the range 20 to 70%.

The water-soluble complexes of bismuth described above have some colouring effect on hair by themselves, but this effect is very much enhanced by the presence of thiosulphate. Compositions of this invention accordingly contain thiosulphate ion in a proportion of 0.2–5%, preferably 1–3% by weight. The thiosulphate may be added as the salt of any inert non-toxic metal, for example as sodium thiosulphate. Ammonium thiosulphate may be used, but is liable to give rise to a smell of ammonia. A preferred alternative is to use the thiosulphate of an amine, such as the amine or alkanolamine described above in connection with the bismuth complex. Amine thiosulphates may readily be prepared by boiling an aqueous mixture of ammonium thiosulphate with an amine having a suitable vapour pressure and water solubility; the resulting aqueous solution can be used without the need to isolate the compound. Solutions of mono-, di- and triethanolamine thiosulphate are particularly convenient to prepare and use in this way. The amine used is additional to that used in forming the water-soluble complex of bismuth and the further proportion included in the composition as described above.

It is possible to include sulphur in the aqueous composition, in addition to the thiosulphate, but this has the disadvantage of incorporating a water-insoluble ingredient. Other conventional ingredients, such as monohydric alcohols, perfumes, thickening agents and surface active agents, may be used in conventional amounts.

The invention also includes a method of darkening keratinous material by applying to the keratinous material an aqueous composition as described above.

The following examples illustrate the invention. Examples 1 to 5 describe the preparation of water-soluble complexes of bismuth. The remaining examples describe compositions according to the invention.

EXAMPLE 1

Bismuth carbonate (5.0 g) and ethylenediamine tetracetic acid (6.25 g) are suspended in 120 ml water and the mixture is heated with stirring at not less than 60° C. until effervescence ceases. Triethanolamine (about 5.0 g) is then added slowly with continued stirring to produce a solution with a pH of about 8.0. The solution, which contains a small quantity (about 0.01 g) of insoluble residue, is cooled to room temperature and filtered from the insoluble residue. The filter is washed with a little water and the washings added to the main filtrate which is then diluted to 200 ml with water.

EXAMPLE 2

A mixture of bismuth carbonate (10 g) and ethylenediamine tetracetic acid (12.5 g) in water (60 ml) is treated as in Example 1, the final filtered solution being diluted to 100 ml. 9.5 g of triethanolamine was used in this preparation and the insoluble residue weighed 0.03 g.

EXAMPLE 3

Proceed essentially as in Example 1 above, but using 6.8 g of nitrilotriacetic acid in place of the ethylenediamine tetracetic acid.

EXAMPLE 4

Bismuth carbonate (5.0 g) and ethylenediamine tetra tetracetic acid (6.25 g) are suspended in 60 ml water and the mixture is heated to about 60° C. with stirring while monoethanolamine is added dropwise to about pH 6. Heating and stirring are continued until effervescence has virtually ceased and then monoethanolamine is again added until the pH has risen to about 9.7 when nearly all the solid matter will have dissolved. The mixture is then cooled to room temperature and filtered from the insoluble residue (about 0.1 g). The residue is washed as in Example 1 and the final solution is diluted to 100 ml. About 3 g of monoethanolamine was used in this preparation.

EXAMPLE 5

Proceed essentially as in Example 4 but using diethanolamine instead of monoethanolamine. The final pH is about 9.1.

EXAMPLE 6

To 10 ml. of the solution prepared according to Example 1 there is added, with stirring, a mixture of nonyl phenol ethoxylate (9 mole) (hereafter referred to as NP9) (0.5 g), triethanolamine (3 g), glycerol (15 g) and isopropyl alcohol (6 ml). To this solution is then added a solution of sodium thiosulphate (3 g) in water (20 ml) and the whole is diluted to 100 ml with water. This solution contains 1.37% as thiosulphate ion and has a pH of approximately 9.5.

This composition darkens hair gradually with successive applications.

EXAMPLE 7

To a mixture of NP9 (0.5 g), triethanolamine (3 g) and isopropyl alcohol (6 ml) and water (10 ml) add 2.5 ml of the solution prepared as described in Example 2. To this mixture then add propylene glycol (60 g) followed by a solution of sodium thiosulphate (5 g) in water (15 ml). Stir the solution and dilute to 100 ml with water. This formula contains 2.26% as thiosulphate ion.

This composition darkens hair significantly with one application.

EXAMPLE 8

To a solution of NP9 (0.5 g), triethanolamine (3 g), perfume (0.2 g) and glycerol (20 g) in ethyl alcohol (20 ml) add, with stirring, 10 ml of the solution prepared as described in Example 1 followed by a solution of sodium thiosulphate (5 g) in water (20 ml). To the final mixture add a solution of hydroxyethylcellulose (0.1 g) in water (10 ml) and dilute the whole to 100 ml.

EXAMPLE 9

To a solution of NP9 (0.5 g), triethanolamine (8 g), glycerol (20 g) and isopropyl alcohol (6 ml) in water (20 ml) add, with stirring, 10 ml of the solution prepared as described in Example 1 followed by a solution of sodium thiosulphate (5 g) in water (20 ml). Dilute the resulting mixture with water to 100 ml.

EXAMPLE 10

Following the procedure described in Example 9, use 10 ml of the solution prepared as described in Example 3 in place of that described in Example 1 and 3 g triethanolamine rather than 8 g. Also before final dilution with water to 100 ml add 2 g finely divided sulphur.

This composition will darken hair at a faster rate than will a similar composition which does not contain sulphur.

EXAMPLE 11

Follow the procedure described in Example 6, but use 3 g diethanolamine instead of triethanolamine. The appropriate pH of the final solution is 11.0.

EXAMPLE 12

To a mixture of NP9 (0.5 g), isopropyl alcohol (6 ml), triethanolamine (9 g) and propylene glycol (55 g) add, with stirring, 10 ml of the solution prepared as described in Example 1 followed by ammonium thiosulphate (3 g) and dilute the mixture to 100 ml.

This composition acts similarly to that of Example 7.

EXAMPLE 13

To a solution of ammonium thiosulphate (30 g) in water (120 ml) add triethanolamine (60 g). Heat the mixture to boiling and continue to boil till the total weight is reduced to about 150 g when most of the ammonia released will have been driven off. The pH of this mixture is about 8.5. To this solution, at room temperature, is then added, with stirring, a mixture comprising 50 ml of the solution prepared as described in Example 2 a polyethanoxyl alkyl ether containing a nominal eight molecules of ethylene oxide (hereinafter referred to as KA8 (5 g), triethanolamine (30 g), propylene glycol (400 g) and isopropyl alcohol (60 ml). The whole is then diluted to 1 liter with water. The solution contains 2.3% as thiosulphate ion.

This composition acts similarly to that of Example 7.

EXAMPLE 14

Heat a solution of ammonium thiosulphate (30 g) and triethanolamine (60 g) in water (120 ml) as described in Example 13 and dilute the final concentrated mixture to 150 ml. Add an aliquot (15 ml) of this solution with stirring to a mixture of NP9 (0.5 g), isopropyl alcohol (6 ml) and propylene glycol (55 g) and to the resulting solution add 10 ml of the solution prepared as described in Example 1. Dilute the resulting mixture with water to 100 ml.

This composition will darken hair or wool by immersion to a marked degree.

EXAMPLE 15

To a mixture of KA8 (0.5 g), triethanolamine (3 g), propylene glycol (45 g) and perfume (0.2 g) in ethanol (12 ml) add, with stirring, 10 ml of the solution prepared as described in Example 2 followed by 15 ml of the solution prepared from ammonium thiosulphate and triethanolamine as described in Example 14.

EXAMPLE 16

Heat a mixture of ammonium thiosulphate (10 g) and diethanolamine (1.24 g) in water (10 ml) until the mixture has lost 5 g in weight and dilute the resultant solution to 50 ml with water. To 15 ml of this solution add 3 g triethanolamine and proceed then as in Example 14. The final solution contains 2.3% as thiosulphate ion.

This composition performs similarly to that of Example 7.

EXAMPLE 17

Concentrate a mixture of ammonium thiosulphate (10 g) and monoethanolamine (8.24 g) in water (20 ml) by boiling to a final weight of about 21 g. Dilute the concentrate to 50 ml with water and use 15 ml of this solution as described in Example 16. The final mixture contains 2.3% as thiosulphate ion.

This composition performs similarly to that of Example 7.

EXAMPLE 18

Proceed as in Example 14, but use 10 ml of the solution prepared as in Example 3 instead of as in Example 1, and include also 3 g triethanolamine.

This composition performs similarly to that of Example 7.

EXAMPLE 19

To a mixture of KA8 (0.5 g), diethanolamine (3 g), propylene glycol (50 g) and isopropyl alcohol (6 ml) add 5 ml of the solution prepared as in Example 2. Stir and then add 15 ml of the solution prepared from ammonium thiosulphate and triethanolamine as described in Example 14. This mixture has a pH of about 9.5. It gives very good darkening of the hair with one application.

EXAMPLE 20

Proceed as in Example 19 but use monoethanolamine (3 g) in place of diethanolamine. The mixture has a pH of about 10.4 and has a similar action on hair to that of Example 19.

EXAMPLE 21

To a mixture of KA8 (0.5 g), diethanolamine (3 g), propylene glycol (50 g) and isopropyl alcohol (6 ml) add 10 ml of the solution prepared as in Example 5. Stir and then add 15 ml of the solution prepared from ammonium thiosulphate and diethanolamine as described in Example 16. This has pH 9.6 and gives particularly good darkening of the hair with one application.

EXAMPLE 22

To a mixture of KA8 (0.5 g), monoethanolamine (3 g), propylene glycol (50 g) and isopropyl alcohol (6 ml) add 10 ml of the solution prepared as in Example 4. Stir and then add 15 ml of the solution prepared from ammonium thiosulphate and monoethanolamine as described in Example 17. This has pH 10.5 and gives very good darkening of the hair with one application.

Tests on white wool, grey hair tresses and human volunteers have shown that these compositions will darken hair or wool much more rapidly than formulations heretofore described.

Samples kept for six months in glass containers at 40° C. have shown no sign of deterioration and chemical analysis has indicated no change in the thiosulphate.

I claim:

1. Aqueous composition for darkening keratinous material comprising a mixture of a solution of a salt of thiosulphuric acid, with a solution of a complex of bismuth with an amino-polyacetic acid, in the presence of a water-soluble amine, and of a di- or poly-hydroxy humectant.

2. Aqueous composition as claimed in claim 1, comprising from 0.2–5.0% by weight of thiosulphate ion ($S_2O_3^=$), from 0.1 to 5.0% by weight of bismuth (as carbonate), a water-soluble amine to maintain the pH of the composition in range 8–11, and from 5–70% by weight of the humectant.

3. Aqueous composition as claimed in claim 1 wherein the amine is an alkanolamine.

4. Aqueous composition as claimed in claim 3, wherein the alkanolamine is monoethanolamine, diethanolamine or triethanolamine.

5. Aqueous composition as claimed in claim 1, wherein the amino-polyacetic acid is nitrilotriacetic acid or ethylenediamine tetracetic acid.

6. Aqueous composition as claimed in claim 1, wherein the solution of a salt of thiosulphuric acid is provided by a solution of an amine thiosulphate.

7. Aqueous composition as claimed in claim 1, wherein the solution of a salt of thiosulphuric acid is provided by a solution of sodium, potassium or ammonium thiosulphate.

8. Aqueous composition as claimed in claim 1, wherein the humectant is a propylene glycol.

9. Aqueous composition as claimed in claim 8, wherein the propylene glycol is present in an amount of 20–70% by weight.

10. Aqueous composition as claimed in claim 1, wherein the humectant is glycerol.

11. Aqueous composition as claimed in claim 10, wherein the glycerol is present in an amount of 5 to 30% by weight.

12. Aqueous composition as claimed in claim 1, comprising thiosulphate ion in an amount of 1–3% by weight, bismuth (as carbonate) in an amount of 0.1–1.5% by weight, the bismuth being present in the form of a complex with ethylenediamine tetracetic acid in the presence of monoethanolamine, diethanolamine or triethanolamine in an amount to maintain the pH of the composition in the range 8 to 10.5, and propylene glycol in an amount of 35–65% by weight.

13. A method of darkening keratinous material which method comprises applying to the keratinous material the aqueous composition claimed in claim 1.

* * * * *

UNITED STATES PATENT OFFICE
CERTIFICATE OF CORRECTION

Patent No. 4,310,329       Dated January 12, 1982

Inventor(s) David O. Holland

It is certified that error appears in the above-identified patent and that said Letters Patent are hereby corrected as shown below:

Column 1, line 31, "0.21" should read --0.2--.

Column 4, line 66, "(1.24 g) should read --(14.2 g)--.

Signed and Sealed this

Thirtieth Day of March 1982

[SEAL]

Attest:

Attesting Officer

GERALD J. MOSSINGHOFF
Commissioner of Patents and Trademarks